(12) United States Patent
Chin

(10) Patent No.: US 6,506,200 B1
(45) Date of Patent: *Jan. 14, 2003

(54) TISSUE SEPARATION CANNULA AND METHOD

(75) Inventor: Albert K. Chin, Palo Alto, CA (US)

(73) Assignee: Origin Medsystems, Inc., Menlo Park, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/525,197

(22) Filed: Mar. 14, 2000

Related U.S. Application Data

(63) Continuation of application No. 08/914,204, filed on Aug. 18, 1997, now Pat. No. 6,036,714, which is a continuation of application No. 08/502,494, filed on Jul. 13, 1995, now abandoned.

(51) Int. Cl.[7] ................................................ A61B 17/00
(52) U.S. Cl. ........................ 606/190; 606/192; 128/898
(58) Field of Search ................................. 606/190, 192, 606/194; 600/207; 604/23, 26, 96.01; 128/898

(56) References Cited

U.S. PATENT DOCUMENTS

| 207,932 | A | 9/1878 | Alvord |
| 1,727,495 | A | 9/1929 | Wappler |
| 1,867,624 | A | 7/1932 | Hoffman |
| 2,011,169 | A | 8/1935 | Wappler |
| 2,028,635 | A | 1/1936 | Wappler |
| 2,316,297 | A | 4/1943 | Southerland et al. |

(List continued on next page.)

FOREIGN PATENT DOCUMENTS

| DE | 39 42 589 | 7/1991 | |
| EP | 0 642 764 A1 | 9/1994 | ........... A61B/17/34 |
| FR | 1 370 580 | 12/1964 | |
| GB | 2 082 459 | 8/1981 | |
| GB | 2 195 540 | 4/1988 | |
| SU | 510235 | 12/1893 | |
| SU | 1371689 | 3/1989 | |

OTHER PUBLICATIONS

Fogarty, M.D., Thomas J.; Scott, M.D., J. Stephen; De La Torre, M.D., Roger; Denes, M.D., Bela S.; and Hermann, George D.; Selected Applications Of Balloon Dissection, Pages 45–52.

Moazami, M.D., Nader; Schimenti, P.A., Elizabeth; Argenziano, M.D., Michael; and Oz, M.D. Mehmet C.; Minimally Invasive Greater Saphenous Vein Harvesting For Cornoary Artery Bypass Surgery, Mar. 1997; Pages 94–98.

DeLaria, G.A., et al., "Leg Wound Complications Associated With Coronary Revascularization," *J. Thorac. Cardiovasc. Surg.*, 81:403–407, 1981.

(List continued on next page.)

*Primary Examiner*—David O. Reip
*Assistant Examiner*—Julian W. Woo
(74) *Attorney, Agent, or Firm*—Fenwick & West LLP

(57) ABSTRACT

A cannula includes a tubular body having proximal closed end and distal blunt end, at least one lumen extending the length of the body, an endoscope having a lighted, viewing end disposed in the lumen near the distal end of the body, and a transparent, tissue separating member substantially covering the distal end of the body. The tissue separating member has a blunt tip disposed from and of the end distal to the body. A method of using such a cannula separates tissue to form an elongated cavity along the course of a small blood vessel and subsequently harvesting the blood vessel.

6 Claims, 4 Drawing Sheets

U.S. PATENT DOCUMENTS

| | | |
|---|---|---|
| 2,868,206 A | 1/1959 | Stoesser |
| 2,944,552 A | 7/1960 | Cannon |
| 3,185,155 A | 5/1965 | Slaten et al. |
| 3,336,916 A | 8/1967 | Edlich |
| 3,357,433 A | 12/1967 | Fourestier et al. |
| 3,856,016 A | 12/1974 | Davis .......................... 128/325 |
| 3,882,854 A | 5/1975 | Hulka et al. ................... 128/6 |
| 3,934,115 A | 1/1976 | Peterson ..................... 219/223 |
| RE29,088 E | 12/1976 | Shaw ..................... 128/303.17 |
| 4,271,839 A | 6/1981 | Fogarty et al. ............. 128/344 |
| 4,318,410 A | 3/1982 | Chin .......................... 128/325 |
| 4,479,497 A | 10/1984 | Fogarty et al. ............. 128/344 |
| 4,493,711 A | 1/1985 | Chin et al. .................. 604/271 |
| 4,526,175 A | 7/1985 | Chin et al. .................. 128/344 |
| 4,630,609 A | 12/1986 | Chin .......................... 128/344 |
| 4,779,611 A | 10/1988 | Grooters et al. ................ 128/4 |
| 4,784,133 A | 11/1988 | Mackin ................... 128/303.1 |
| 4,863,440 A | 9/1989 | Chin .......................... 604/271 |
| 4,921,483 A | 5/1990 | Wijay et al. .................. 604/96 |
| 5,163,949 A | 11/1992 | Bonutti ...................... 606/192 |
| 5,183,464 A | 2/1993 | Dubrul et al. ................. 128/3 |
| 5,271,380 A | 12/1993 | Riek et al. ...................... 128/4 |
| 5,331,975 A | 7/1994 | Bonutti ...................... 128/898 |
| 5,334,150 A | 8/1994 | Kaali .......................... 604/164 |
| 5,373,840 A | 12/1994 | Knighton ........................ 128/4 |
| 5,376,076 A | 12/1994 | Kaali .......................... 604/164 |
| 5,496,345 A | 3/1996 | Kieturakis et al. .......... 606/192 |
| 5,514,153 A | 5/1996 | Bonutti ...................... 606/190 |
| 5,540,711 A | 7/1996 | Kieturakis et al. .......... 606/192 |
| 5,551,947 A | 9/1996 | Kaali .......................... 606/264 |
| 5,569,291 A | 10/1996 | Privitera et al. ............ 606/185 |
| 5,569,292 A | 10/1996 | Scwemberger et al. ..... 606/185 |
| 5,591,192 A | 1/1997 | Privitera et al. ............ 606/185 |
| 5,601,589 A * | 2/1997 | Fogarty et al. ............. 606/192 |
| 5,607,441 A * | 3/1997 | Sierocuk et al. ............ 606/190 |
| 5,613,947 A | 3/1997 | Chin ........................... 604/96 |
| 5,653,726 A | 8/1997 | Kieturakis ................... 606/190 |
| 5,667,520 A | 9/1997 | Bonutti ....................... 606/190 |
| 5,685,820 A | 11/1997 | Riek et al. ................... 600/114 |
| 5,702,417 A * | 12/1997 | Hermann ..................... 606/194 |
| 5,730,756 A | 3/1998 | Kieturakis ................... 606/190 |
| 5,738,628 A | 4/1998 | Sierocuk et al. ............ 600/104 |
| 5,762,604 A | 6/1998 | Kieturakis ................... 600/115 |
| 5,772,680 A | 6/1998 | Kieturakis et al. .......... 606/190 |
| 5,860,997 A | 1/1999 | Bonutti ....................... 606/190 |
| 6,036,714 A * | 3/2000 | Chin .......................... 606/190 |

OTHER PUBLICATIONS

Dimitri, W.R., et al., "A Quick And Atraumatic Method Of Autologous Vein Harvesting Using The Subcutaneous Extraluminal Dissector," *J. Cardiovasc. Surg.,* 28:103–11, 1987.

Hauer, G., et al., "Endoscopic Subfascial Discission Of Perforating Veins," *Surg. Endosc.,* 2:5–12, 1988.

Meldrum–Hanna, W., et al., "Long Saphenous Vein Harvesting," *J. Surg.,* 56:923–924, 1986.

Moazami, N., M.D., et al., "Minimally Invasive Greater Saphenous Vein Harvesting For Coronary Artery Bypass Surgery," *Surgical Rounds,* pp. 94–98, Mar. 1997.

Rashid, A., et al., "Subcutaneous Technique For Saphenous Vein Harvest," *Ann. Thorac. Surg.,* 37(2):169–170, 1984.

Wheatley, D.J., M.D., ed., "Surgery of Coronary Artery Disease," C.V. Mosby Company, pp. 348–349, pp. 374–375.

"Incision Decision," Atrium Medical Corporation advertisement, appearing in *J. Thorac. Cardiovasc. Surg.,* 83(4), 1982.

"Saphenous Vein Grafts Are No. 1. Period," Atrium Medical Corporation advertisement, appearing in *J. Thorac. Cardiovasc. Surg.,* 82(6), 1981.

* cited by examiner

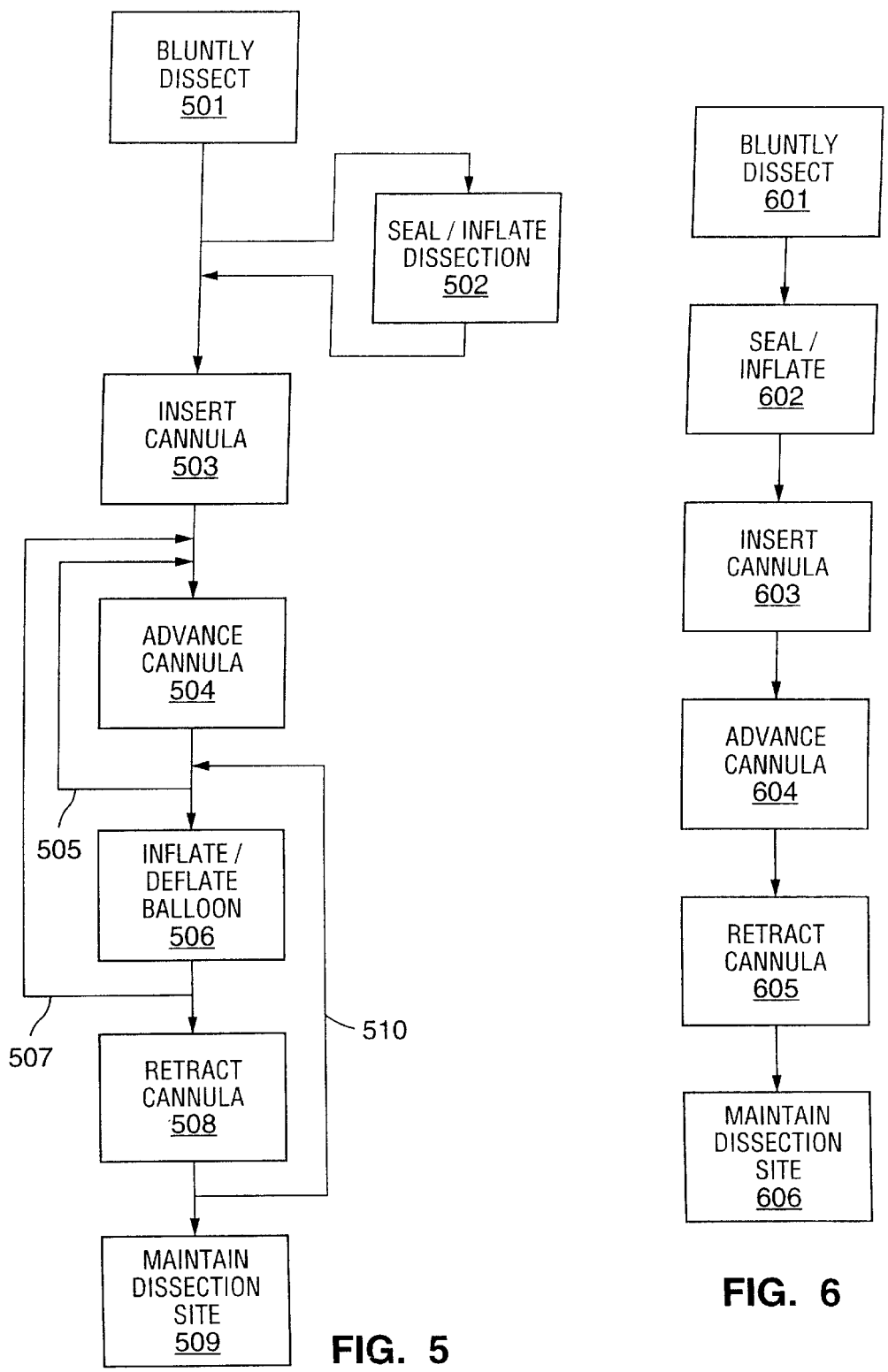

TISSUE SEPARATION CANNULA AND METHOD

This is a continuation of application Ser. No. 08/914,204, filed Aug. 18, 1997, now U.S. Pat. No. 6,036,714, issued Mar. 14, 2000; which was a continuation of application Ser. No. 08/502,494, filed Jul. 13, 1995, now abandoned.

RELATED APPLICATION

The subject matter of this application is related to the subject matter of application Ser. No. 08/421,481 entitled "CANNULA ASSEMBLY AND METHOD FOR PROGRESSIVELY DISSECTING TISSUE" filed on Apr. 12, 1995 by Albert K. Chin, that is assigned to the assignee as the present application and is incorporated herein by reference in its entirety.

BACKGROUND OF THE INVENTION

1. Field of the Invention

The present invention relates generally to a tissue separation cannula used for forming an elongated cavity in tissue planes particularly along the course of a small blood vessel, and more specifically relates to a cannula having an endoscope for continuously visualizing the blunt dissection site through a tissue separating member which is transparent and has a tapered shape.

2. Description of Background Art

Present methods for the formation of an elongated cavity involve the use of blunt probes that are pushed through body tissue to accomplish the tissue dissection. The force exerted by the passage of mechanical probes may lead to blood vessel avulsion and trauma to tissue and internal organs.

The problem becomes acute when dissecting and harvesting blood vessels having a small diameter of about 3 to 8 mm. The techniques which are used for dissection of larger blood vessels such as the aorta are not applicable since the aorta is located in the retroperitoneum bounded by the peritoneum on one side and the psoas muscle on the other side. An everting balloon placed in the infrarenal space located just below the kidney will track easily down the length of the aorta along a natural cleavage plane when inflated.

An everting type of balloon encounters difficulties when dissecting tissue adjacent a smaller-diameter vessel. This is due to the presence of less distinct planes that exist between small diameter blood vessels and the tissue that surrounds these vessels. as compared with the aorta and the tissue that surrounds the aorta. For example, if an everting balloon is placed adjacent to the saphenous vein in the leg, it usually skews dissection upon inflation rather than track along the vein. This is due to the amorphous nature of the fat and connective tissue that surrounds the saphenous vein.

Everting balloon catheters are known which are used for arterial dilation. (See. for example, U.S. Pat. No. 4,479,497 (Fogarty et al., Oct. 30, 1984) and U.S. Pat. No. 4,863,440 (Chin. Sep. 5, 1989)).

Double lumen everting balloon catheters, such as those disclosed in the Fogarty et al. '497 and the Chin '440 patents, have a through-lumen that slidably receives an endoscope. However, an endoscope used in conjunction with those disclosed catheters is unable to monitor the dissection process, since the endoscope lies within the central lumen proximal to the everting balloon. As the balloon everts from the catheter, the internal inflation pressure squeezes the walls of the balloon and closes off the distal viewing channel. Also, the area that requires monitoring during balloon dissection is located at the advancing front of the everting balloon. This area corresponds to the balloon/tissue interface that is subject to forces which cause tissue separation. Thus an endoscope in the central lumen of existing double-lumen. everting balloon catheters is unable to view the area of tissue separation, since a double layer of balloon membrane lies between the endoscope and the tissue and blocks the endoscopic line of sight This double layer obscures and distorts the viewing area of tissue separation.

Endoscopes have been disclosed for use in optical trocars such as in U.S. Pat. No. 5,385,572 (Nobles et al., Jan. 31, 1995) and EP 0 642 764 A1 (Sauer et al., published Mar. 15, 1995) and in harvesting blood vessels such as in U.S. Pat. No. 5,373,840 (Knighton, Dec. 20, 1994). The Nobles et al. '572 patent and the Sauer et al. '764 application disclose the use of sharp-tipped, metal cutting elements which extend outwardly from an endoscope positioned in the trocar. Control of the dissection is difficult because visualization of the vessel is obscured by the collapse of the tissue planes into the area between the cutting element and the endoscope. Furthermore, the risk of side vessel avulsion or trauma to the vessel is greatly increased by the orientation of the outwardly extending cutting elements.

The endoscope disclosed in Knighton '840 has a lateral dimension of a size sufficient to accommodate the blood vessel being harvested and at least one tool for use in harvesting the blood harvested. However, the failure of the endoscope to enlarge a cavity adjacent the blood vessel obscures viewing of the dissection area and manipulation of the vessel therein. The position of the viewing image relative to the tissue dissection area could obscure the identification of side vessels leading to an increased risk of vessel avulsion. Since the vessel is retrieved through the center of the endoscope, all side vessels must be severed for the endoscope to advance and the length of the vessel thus retrieved is limited substantially by the length of the body of the endoscope.

SUMMARY OF THE INVENTION

The present invention provides a cannula for bluntly dissecting an elongated cavity in tissue particularly along the course of a vessel. The cannula includes a tubular body having proximal closed end and distal blunt end and at least one lumen extending the length of the body. The cannula also includes an endoscope having a lighted, viewing end disposed in the lumen near the distal end of the body, and includes a transparent, tissue separating member substantially covering the distal end of the body. The tissue separating member has a blunt tip disposed towards the distal end of the body.

A method is also disclosed for bluntly dissecting an elongated cavity particularly along the course of a vessel using a cannula. The method includes the steps of: bluntly dissecting an initial cavity; separating the tissue by advancing the cannula along the cavity with continuous, visual observation; repeating the prior step of separating the tissue at least until the cavity is sufficiently elongated to advance a balloon therein; and successively inflating and deflating a balloon within the cavity to enlarge the cavity along the course of the vessel. The method further may include removing the cannula, then maintaining the elongated cavity using insufflated gas through a balloon cannula that seals the incision against gas leakage, or using a structural balloon, or a mechanical structural support.

In another embodiment of the present invention, the method includes the steps of bluntly dissecting an initial cavity; sealing and inflating the cavity; and separating the tissue along the cavity assisted by continuous, visual observation while under inflation until the cavity is sufficiently elongated.

The isolated vessel such as the saphenous vein, may be harvested and removed for use as a coronary artery or vascular graft, or may be left in place as an in-situ femoropopliteal or femoral-distal graft. The side branches of the vein are ligated, clipped, or occluded in both applications. In the case of an in-situ graft, the valves in the vein are disrupted by means of a valvulotome.

BRIEF DESCRIPTION OF THE DRAWINGS

FIG. 5 is a flowchart of one embodiment of the method of separating tissue using the cannula of the present invention;

FIG. 6 is a flowchart of another embodiment of the method of the separating tissue.

DESCRIPTION OF THE PREFERRED EMBODIMENT

In accordance with one embodiment of the present invention, a cannula includes a tubular body having proximal closed end and distal blunt end, at least one lumen extending the length of the body, an endoscope having a lighted, viewing end disposed in the lumen near the distal end of the body, and a transparent, tissue separating member substantially covering the distal end of the body and having a blunt tip towards the end distal to the body. The present invention also includes a method of using such a cannula for separating tissue to form an elongated cavity along the course of a small blood vessel and subsequently harvesting the blood vessel, or using the blood vessel as an in-situ graft.

Figure 1:
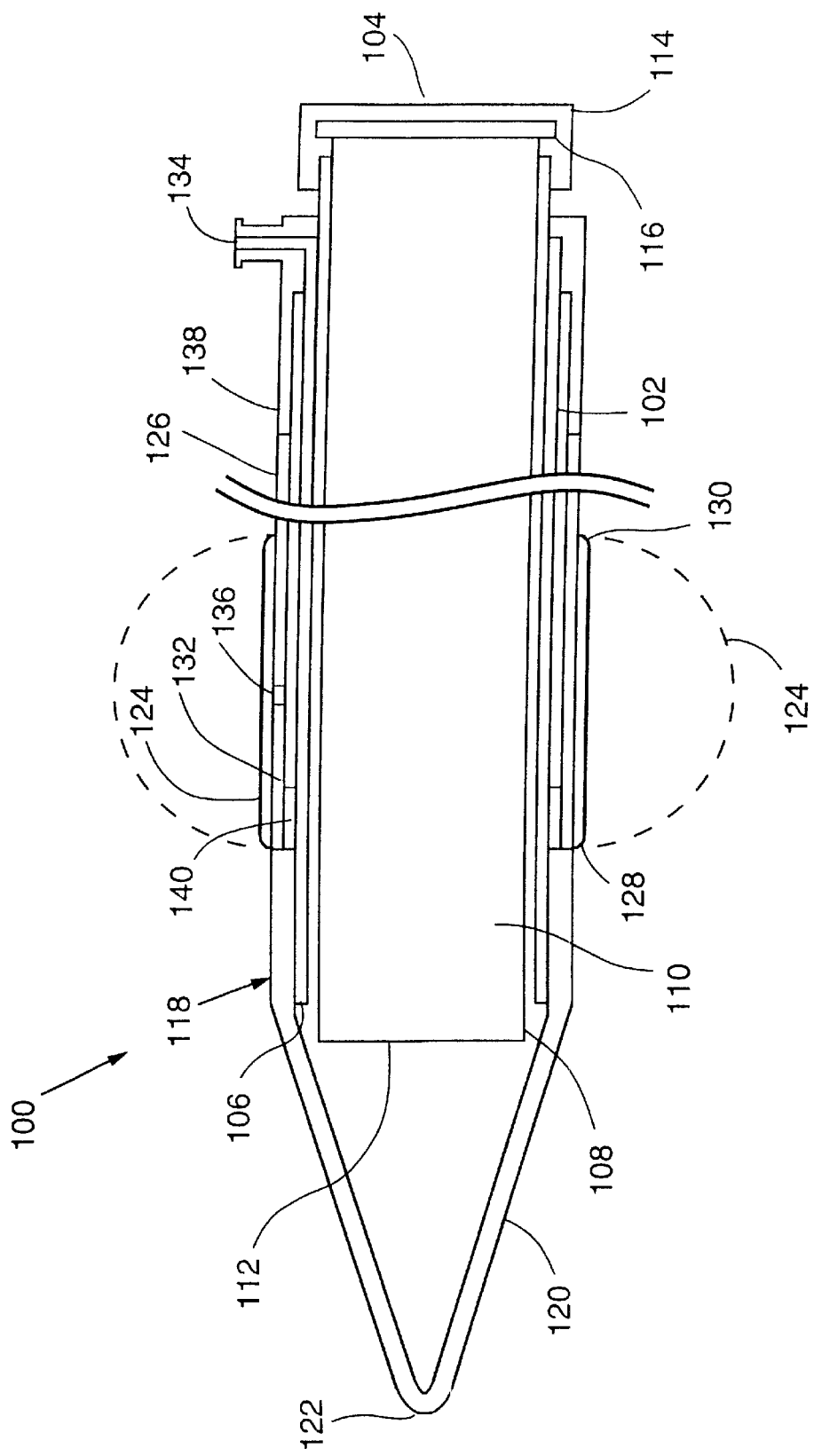
FIG. 1 is a partial, longitudinal cross-section view of a cannula of the present invention illustrating the profile of a tissue separating member affixed thereto.

FIG. 1 shows an embodiment of the cannula 100 of the present invention. The cannula 100 includes a tubular body 102 having a proximal end 104 and a distal end 106. At least one lumen 108 extends the length of the body 102. Disposed in the lumen 108 is an endoscope 110 having a lighted, viewing end 112 near the distal end 106 of the body. The other end of the endoscope 110 has a proximal end cap 114 and an elastomeric washer 116 that provides a pressure-sealed, sliding fit with the endoscope.

The cannula 100 also includes a transparent, tissue separating member 118 substantially covering the distal end 106 of the body. The shape of the tissue separating member 118 has a tapered section 120 which angles towards a blunt, tissue separating member tip 122 distal to the distal end 106 of the tubular body. The shape of the tissue separating member 118 allows atraumatic dissection of a cavity with sufficient control and maneuvering to prevent tearing or puncturing of the nearby vessel. The tapered shape and blunt tip of the tissue separating member 118 also allows deflection of side vessels to the side of the cannula 100 without their avulsion, upon forward advancement of the cannula 100.

Figure 2:
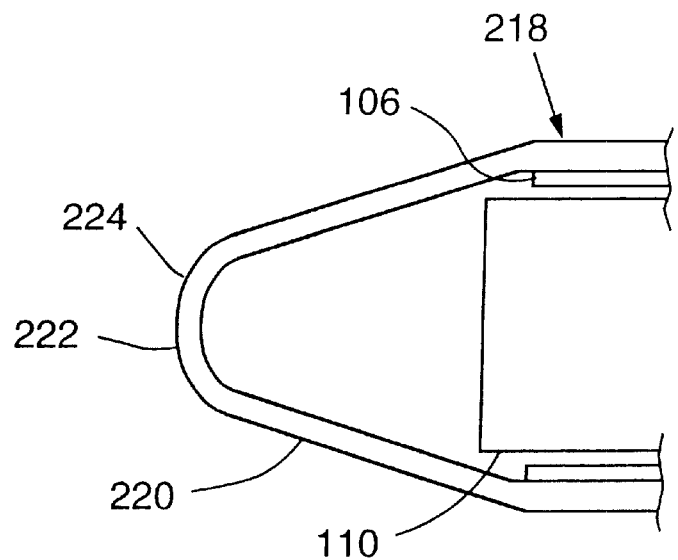
FIG. 2 is an isolated, cross-section view of another embodiment of the tissue separating member having a blunt spherical tip with a straight tapered section suitable for use with the cannula of the present invention.

Alternative embodiments of the present invention include other shapes for the tissue separating member 118 which provide the necessary control and atraumatic dissection. FIG. 2 illustrates another embodiment of a tissue separating member 218 which substantially covers the distal end 106 of the cannula and provides a transparent shield for the endoscope 110. The tissue separating member 218 includes a tapered section 220 integrally formed with a more blunt, spherical section 224 at the distal tip 222 of the tissue separating member.

Figure 3:
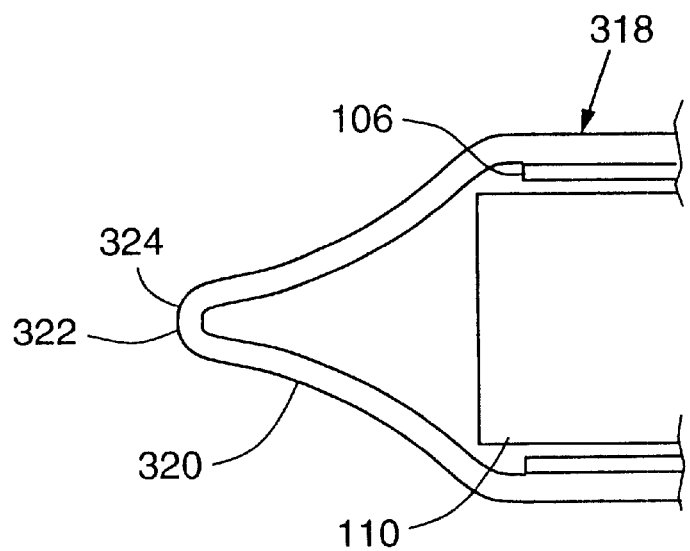
FIG. 3 is an isolated, cross-section view of another embodiment of the tissue separating member having a blunt tip with a curved tapered section suitable for use with the cannula of the present invention.

FIG. 3 illustrates another embodiment of a tissue separating member 318 which substantially covers the distal end 106 of the cannula and provides a transparent shield for the endoscope 110. The tissue separating member 318 includes a curved tapered section 320 integrally formed with a blunt section 324 at the distal tip 322 to form a duck-bill shape. The curved tapered section 320 can have convex or concave shape.

Figure 4:
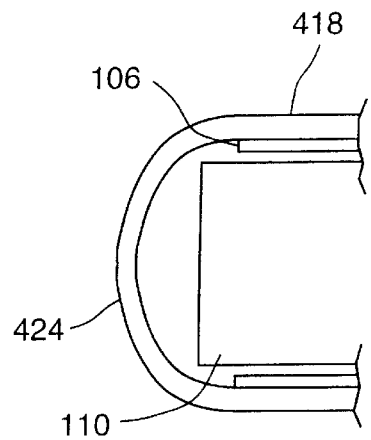
FIG. 4 is an isolated, cross-section view of another embodiment of the tissue separating member having a hemispherical shape suitable for use with the cannula of the present invention.

FIG. 4 illustrates another embodiment of a tissue separating member 418 which substantially covers the distal end 106 of the cannula and provides a transparent shield for the endoscope 110. The tissue separating member 418 has a hemispherical shape 424 covering the distal end 106.

Preferably, the tissue separating members 118, 218 have an overall length of about 0.5 inches and a uniform wall thickness of about 0.06 inches along the entire surface to allow visualization by the endoscope without distortion of the image that would result if a section of the wall is thickened or otherwise forms a lens. The wall thickness of the tissue separating member may be contoured to form a lens for special applications that require a magnified or otherwise distorted image, e.g. asymmetric, fish-eyed, etc. transmitted by the endoscope. A suitable material for making the tissue separating member is polycarbonate. Any material which is sufficiently strong to separate tissue and sufficiently transparent to allow visualization by the endoscope is suitable for use in the present invention.

Referring to FIG. 1, the cannula 100 preferably includes a balloon 124 located at the distal end 106 on the exterior wall 126 of the cannula. The balloon 124 may be elastic or inelastic although an elastomeric balloon is preferred because it achieves a smaller, smoother outer profile. Fully inflated (as shown in phantom 128 in FIG. 1), the diameter of the balloon 124 is about 3 cm. Preferably, a sleeve type of balloon is used as the balloon 124 wherein both the distal end 128 and proximal end 130 of the balloon are secured to the exterior wall 126 of the cannula.

The inflation of the balloon 124 is provided by connection to another lumen 132 which provides a pressurized fluid, such as a gas or liquid, from an inflation port 134 to a hole 136 in the exterior wall 126 of the cannula within the proximal and distal ends 130, 128 of the balloon to communicate with the interior thereof. A plunger device, such as a manually-operated syringe, is suitable for connecting at the inflation port 134 to control the inflation of the balloon 124. The other lumen 132 is formed as another tubular body 138 in a concentric arrangement with the body 102 to form a space 140 between the two bodies. Another embodiment suitable of the present invention may include two lumens 108, 132 in a side-by-side arrangement. Additional lumens can be added in a similar fashion to provide other functions such as irrigation and aspiration in known manner.

The present invention is illustrated using a sleeve type of balloon with the cannula 100. Other balloon types are suitable for use with the present invention such as, and not limited to, using an investable balloon positioned in a separate lumen in the cannula to assist in separating the tissue when inflated.

The cannulae 100 may be manufactured from a variety of bioinert, substantially inelastic materials, such as polyethylene, polyurethane, polyvinyl chloride, polyimide plastic, and the like that preferably have a tensile strength of at least 10,000 psi. Preferably, each lumen of the cannula 100 has a wall thickness of between about 0.005 inch and 0.010 inch.

The endoscope 110 has an outer diameter of approximately 5.0 mm. The endoscope may be permanently built into the cannula 100, or it may be a separate device that is advanced through the endoscope lumen 108. The endoscope 110 is positioned within the lumen 108 with the tip in correct position to allow unimpeded visualization of the surrounding tissue and vessel outside of the cannula 100. A preferred endoscope 110 having a tubular diameter of about 5.0 mm is commercially available from Solos Endoscopy, Inc., at Norcross, Ga. However, other commercially available endoscopes 110 that may be used in practicing the present invention include those which are as small as 1.00 to 1.75 mm in diameter.

Methods for bluntly dissecting an elongated cavity using the cannula of the present invention are shown in the flow diagrams of FIGS. 5 and 6. Although the blunt dissection of an elongated cavity along the course of a vessel is specifically described, the present invention is generally applicable for separating any tissue. For example, the cannula may be used to track along the median nerve from an incision at the patient's wrist, forming a cavity for surgical treatment of carpal tunnel syndrome. The cannula allows visualization and tracking of the median nerve, preventing the injury to the nerve which may occur if blind advancement of a balloon cannula were used.

The method in FIG. 5 includes the steps of incising the skin and bluntly dissecting 501 through the subcutaneous issue to the level of the vessel. Blunt dissection is performed to separate the vessel from adjacent tissue for a length of approximately 1 to 2 cm. The blunt dissection may be performed with a pair of curved Metzenbaum scissors, using the tips of the scissors to cut and bluntly spread tissue in a plane between the vessel and the adjacent tissue.

Preferably, a blunt tip balloon cannula is introduced into the space between the vessel and the overlying tissue. The balloon is then inflated to form a gastight seal which seals 502 the dissection. A gas such as carbon dioxide is infused under pressure via the blunt tip balloon cannula. The natural perivascular plane around the vessel is expanded by the injected gas, for a tract along the course of the vessel. For a superficial vessel such as the saphenous vein, the expanded track is visible on the surface of the skin. The interior of the expanded tract is not cleanly open but rather, includes gossamer-like strands of connective tissue and fat, preventing unobstructed visualization and making hazardous the passage of an endoscope along the track adjacent to the vessel. If a conventional endoscope is pushed into this connective tissue in an attempt to form a cavity adjacent to the vessel, the view through the conventional endoscope is blurred by the tissue that contacts the viewing end of the conventional endoscope. A blurred view through the conventional endoscope increases the potential for side branch avulsion during blunt dissection of the perivascular tunnel.

The cannula 100 is inserted 503 into this dissected space. With the fiberoptic endoscope 110 continuously visualizing down the course of the vessel, the cannula 100 separates the tissue by advancing forward 504, probing between the vessel and the adjacent gossamer perivascular tissue in the plane initiated by blunt dissection. The transparent, tissue separating member 118 allows the endoscope 110 to clearly visualize a segment of the vessel at least equivalent to the length of the tapered section 120.

If the blunt dissection along the course of the vessel is not sufficient to advance the balloon 124 therein, the method returns 505 to the step of advancing the cannula 504 forward to continue the separation of tissue along the course of the vessel. When a cavity of sufficient length has been formed by the cannula 100, the balloon 124 is advanced into the cavity and is successively inflated and deflated 506 to enlarge the cavity to about 3 cm in diameter.

The method returns 507 to the step of separating the tissue by advancing the cannula 504 and the step of selectively inflating and deflating 506 the balloon 124, as described above. Successive application of these steps forms a cavity along the entire length of the vessel. Once the elongated cavity is complete, the cannula 100 is completely retracted 508 from the elongated cavity.

The elongated cavity site is then maintained 509 in expanded form in accordance with the method of the present invention. Following use of the cannula 100 to form an elongated cavity along the course of a vessel, the cavity must be supported to allow procedures to be performed on the vessel, such as vessel dissection, grafting of the vessel, or vessel harvesting. A blunt tip trocar may be used to seal the entrance incision and allow gas insufflation to maintain the cavity in expanded form. One blunt-tip balloon trocar suitable for use herein is presently marketed by Origin Medsystems, Inc. of Menlo Park, Calif.

Another method of maintaining the cavity in expanded form includes making an incision at the distal extent of the dissected cavity, and inserting a double rod system through the cavity. The double rods are suspended via a laparoscopic mechanical lifting device to maintain the cavity. This system allows instruments to be advanced into the cavity via simple incisions, without the requirement for trocars with gas sealing valves, as is the case with gas insufflation.

Alternatively, an inflatable structural balloon or mechanical structure may be used to support the dissected cavity. For example, the cavity may be maintained by mechanical retraction or by a mechanical finger-like retractor attached to a powered lifting arm plus a separate flat balloon retractor used to displace the side wall of the cavity. The endoscope 110 may be introduced behind the legs of the finger-like retractor that connect to the mechanical lifting arm.

The vessel is completely dissected within the formed cavity, using laparoscopic instruments such as graspers, scissors, hooks, and blunt probes. Side branches to the vessel may be ligated using suture ties, clipped using titanium vessel clips, cauterized using electrocautery, or a combination of these procedures. The dissected vessel is removed from the cavity for possible use as a conduit for an arterial bypass procedure, or the vessel may be left in place to be used as an in-situ bypass graft.

In an alternate embodiment, the method forms a small diameter cavity, about 7 mm, along the entire length of the vessel before the cavity is then enlarged. As illustrated in FIG. 5, the steps of making a blunt dissection 501, sealing and inflating the dissection 502, inserting 503 the dissection cannula 100 and successively separating the issue by advancing 504 the cannula 100 are performed as described above. The alternate method, however, continues advancing 504 the dissection cannula until the entire length of the elongated cavity is bluntly dissected to the small diameter of about 7 mm.

Only after the entire length of the elongated cavity has been bluntly dissected does the alternate method include the step of inflating and deflating 506 the balloon 124 of the cannula to increase the diameter of the distal end of the elongated cavity to about 3 cm. The dissection cannula 100 is then retracted 508 partially by about the length of the balloon 124. The alternate method then returns 510 to the steps of inflating and deflating 506 the balloon 124. The cannula 100 is again retracted 508 partially and the method returns 510 to repeating the above steps until the entire length of the elongated cavity has been enlarged to the diameter of the inflated balloon 124 which is typically about 3 cm.

An alternate method involves making an incision down to the vessel. Blunt dissection of the vessel from the adjacent tissue is performed for a 3–4 cm length. A blunt tip trocar is placed in the incision, and gas insufflation is initiated.

The cannula 100 is inserted through the blunt tip trocar, and blunt dissection using the balloon 124 is performed under the presence of gas insufflation in the cavity. This technique provides a larger cavity for visualization during separation of the tissue, since gas insufflation is used from the onset of blunt dissection. However, a gas sealing blunt tip trocar is required. If vessel dissection without gas insufflation is conducted, and a double rod system is used to maintain the cavity, then the use of a blunt tip trocar may be avoided.

Another method of the present invention forms a small diameter cavity along the entire length of the vessel. The cavity is enlarged only by the initial inflation at the blunt dissection site. As illustrated in FIG. 6, the steps of making a blunt dissection 601, sealing and inflating the dissection 602, inserting 603 the cannula 100, and successively separating the tissue by advancing 604 the cannula 100 are performed as described above. The cannula advances 604 until the entire length of the elongated cavity is bluntly dissected and expanded only by the inflating gas of the prior step 602. The cannula 100 is then retracted 605 entirely from the elongated cavity. The dissection site is maintained 606 in expanded form as described above.

The present invention includes methods particularly useful for harvesting vein. In one method, an incision is made near the ankle, and the cannula is passed up to the knee, or near the knee. Following balloon inflation to enlarge this segment, an incision is made into the dilated cavity near its endpoint at the knee. The incision at the knee is the approximate mid-point of the saphenous vein between the ankle and the groin. The vein is isolated and the side branches ligated in this segment between the ankle and the knee to harvest and remove this segment.

The segment from the knee to the groin is then harvested. The cannula may be passed from the same knee incision used for harvesting the vein from the lower leg, or a separate incision may be made slightly above the knee. Use of a separate incision may be useful if the vein is overly curved or tortuous as it passes around the knee. The cannula is advanced toward the groin, the balloon is inflated to dilate the cavity, an incision is made into the dilated cavity at its groin end, and the portion of the saphenous vein residing in the thigh is harvested.

As an alternate method for saphenous vein harvesting, the initial incision may be made at the knee. The cannula is passed in both directions, towards the ankle and the groin, from the same incision. Then additional incisions are made at the ankle and at the groin to allow harvesting of the entire length of the saphenous vein. The vein may be removed as a single strand, or it may be cut at the knee and removed as two strands.

In some anatomic regions, it may be difficult to advance a rigid, straight tissue separation device along the course of a vessel. For example and referring to FIG. 7, if the saphenous vein 700 is harvested by passing the cannula 702 from an incision 712 just above the ankle, and the presence of the medial malleolus 704 and the foot 706 may prevent an otherwise rigid cannula from being angled upwards or sideways to follow the vein 700.

Figure 7:
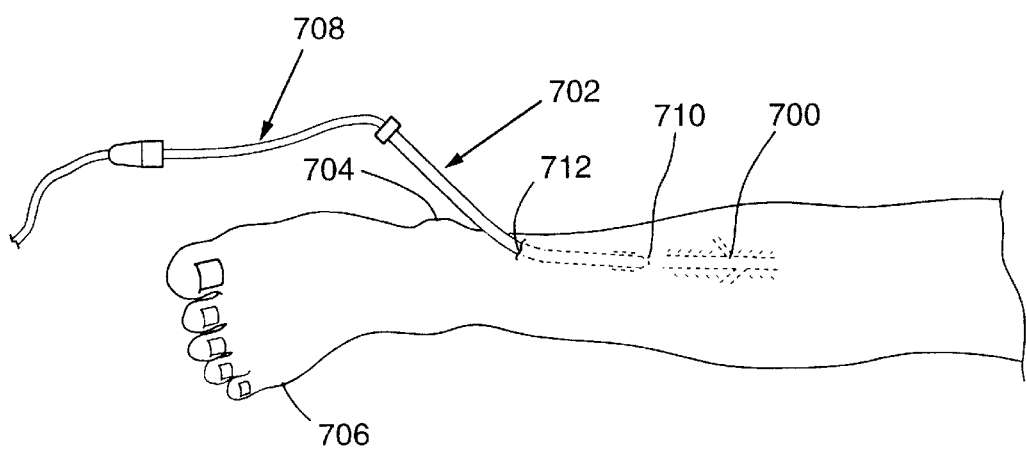
FIG. 7 is a partial side view of a patient's leg with the advancement of a flexible cannula of the present invention through an incision.

For such obstructed situations. the cannula 702 may be formed with a body which is flexible or otherwise malleable, or is rigid with a pre-determined gradual arc, as shown in FIG. 7. The endoscope 708 that is inserted into the cannula 702 up to the tissue separating member 710 must also be flexible to facilitate shaping the flexible body within the curved cannula. Such conventional flexible fiberoptic endoscopes are commonly used in gastrointestinal endoscopy.

What is claimed is:

1. A method for bluntly dissecting an elongated cavity in tissue particularly along the course of a vessel using a cannula having a lumen for receiving an endoscope therein and including a rigid transparent tip disposed to seal a distal end of the lumen and directly contact tissue to be dissected, the cannula having a balloon attached to an exterior wall of the cannula proximal the tip at the distal end of the cannula and being capable of selective radial expansion, the method comprising the steps of:

bluntly dissecting an initial cavity proximate the vessel;

advancing the tip of the cannula along the vessel to separate tissue therefrom in direct contact with the tip under continuous visual observation through the tip to enlarge the initial cavity;

repeating the prior step of separating the tissue at least until the cavity is sufficiently elongated to receive the balloon therein;

sealing and insufflating the initial cavity; and selectively advancing the tip and cannula and inflating and deflating the balloon within the insufflated cavity to extend the cavity along the vessel.

2. The method of claim 1, wherein after the step of selectively inflating and deflating the balloon, the method includes the steps of:

retracting the cannula entirely from the elongated cavity while maintaining the elongated cavity substantially in expanded form under insufflation.

3. The method of claim 1, wherein the method further includes the step of:

dissecting the vessel within the formed elongated cavity.

4. The method of claim 3, wherein the method further includes the step of:

removing the vessel from the elongated cavity.

5. The method of claim 3, wherein the method further includes the step of ligating the side branches of the vessel within the elongated cavity under insufflation.

6. A method for bluntly dissecting an elongated cavity in tissue particularly along the course of a vessel using a cannula having a lumen for receiving an endoscope therein and including a rigid transparent tip disposed to seal a distal end of the lumen and directly contact tissue to be dissected, the cannula having a balloon attached to an exterior wall of the cannula proximal the tip at the distal end of the cannula and being capable of selective radial expansion, the method comprising the steps of:

bluntly dissecting an initial cavity proximate the vessel;

advancing the tip of the cannula along the vessel to separate tissue therefrom in direct contact with the tip under continuous visual observation through the tip to enlarge the initial cavity;

repeating the prior step of separating the tissue at least until the cavity is sufficiently elongated;

sealing and insufflating the initial cavity;

repeating the step of advancing the cannula along the cavity under insufflation until a substantial portion of the cavity is elongated;

retracting the cannula partially within the elongated cavity;

selectively inflating and deflating the balloon within the elongated cavity to expand the dimension of the elongated cavity along at least a portion of the elongated length thereof; and repeating the steps of partially retracting the cannula and selectively inflating and deflating the balloon within the elongated cavity under insufflation until the dimension of the entire elongated cavity is expanded.

\* \* \* \* \*